(12) United States Patent
Wada et al.

(10) Patent No.: US 7,407,557 B2
(45) Date of Patent: Aug. 5, 2008

(54) METHOD FOR PRODUCING DISPOSABLE WEARING ARTICLE

(75) Inventors: Takao Wada, Settsu (JP); Mamoru Itani, Settsu (JP); Shuhei Kurata, Settsu (JP)

(73) Assignee: Zuiko Corporation (JP)

( * ) Notice: Subject to any disclaimer, the term of this patent is extended or adjusted under 35 U.S.C. 154(b) by 482 days.

(21) Appl. No.: 10/538,500

(22) PCT Filed: Dec. 18, 2002

(86) PCT No.: PCT/JP02/13205

§ 371 (c)(1),
(2), (4) Date: Jun. 9, 2005

(87) PCT Pub. No.: WO2004/054490

PCT Pub. Date: Jul. 1, 2004

(65) Prior Publication Data

US 2006/0244166 A1 Nov. 2, 2006

(51) Int. Cl.
- A61F 13/15 (2006.01)
- A61F 13/20 (2006.01)
- B29B 17/00 (2006.01)
- B29C 37/00 (2006.01)
- B32B 38/04 (2006.01)
- B32B 37/00 (2006.01)

(52) U.S. Cl. ........... 156/226; 156/250; 156/253; 156/256; 156/264; 156/265; 264/37.1; 604/385.01; 604/386

(58) Field of Classification Search ........... 156/226, 156/250, 253, 256, 264, 265; 264/37.1; 604/385.01–386
See application file for complete search history.

(56) References Cited

U.S. PATENT DOCUMENTS 5,110,386 A * 5/1992 Ochi et al. ........... 156/204

(Continued)

FOREIGN PATENT DOCUMENTS

JP 9-224973 9/1997

(Continued)

OTHER PUBLICATIONS

English language translation of International Preliminary Examination Report.

*Primary Examiner*—Philip C Tucker
*Assistant Examiner*—Michael N Orlando
(74) *Attorney, Agent, or Firm*—Gerald E. Hespos; Anthony J. Casella

(57) ABSTRACT

A method includes producing an elastic strip material (12) by sandwiching an elastic member (4) between two webs (10, 11) under a stretched state in the longitudinal direction of the webs (10, 11), halving the elastic strip material (12) in the widthwise direction so that protrusions (12a) and recesses (12b) alternately appear, separating a first elastic strip material and a second elastic strip material obtained by halving in the widthwise direction, shifting the phases of the first and second elastic strip materials in the longitudinal direction so that the protrusions and the recesses become in phase, reducing the shrinking force of the elastic member near the protrusions (12a) of the first and second elastic strip materials (12A and 12B), and attaching an absorber (12c) onto parts (12c) of the first and second elastic strip materials (12A) where the shrinking force is reduced.

14 Claims, 14 Drawing Sheets

U.S. PATENT DOCUMENTS

| | | | | |
|---|---|---|---|---|
| 5,342,342 | A * | 8/1994 | Kitaoka | 604/385.19 |
| 5,370,634 | A * | 12/1994 | Ando et al. | 604/385.21 |
| 5,569,234 | A * | 10/1996 | Buell et al. | 604/396 |
| 5,858,151 | A * | 1/1999 | Igaue et al. | 156/164 |
| 6,979,380 | B2 * | 12/2005 | Thorson et al. | 156/259 |
| 2002/0046802 | A1 * | 4/2002 | Tachibana et al. | 156/209 |

FOREIGN PATENT DOCUMENTS

| | | |
|---|---|---|
| JP | 2002/113042 | 4/2002 |
| JP | 2002/253605 | 9/2002 |
| JP | 2002/272781 | 9/2002 |

* cited by examiner

METHOD FOR PRODUCING DISPOSABLE WEARING ARTICLE

TECHNICAL FIELD

The present invention relates to a method for continuously producing disposable wearing articles such as disposable underpants.

BACKGROUND TECHNOLOGY

Body fluid absorbent wearing articles of the disposable underpants type include pants-type diapers, underpants and training pants for infants and small children and incontinence underpants. A method for producing such disposable wearing articles is disclosed, for example, in Japanese Unexamined Patent Publication No. 2002-113042.

What is required for the method for producing disposable wearing articles is to maximally reduce trims (loss parts) produced by cutting webs (sheet-shaped backing materials such as nonwoven fabric) in the production process. This enables the production cost for wearing articles to be decreased.

Further, when a produced disposable wearing article is worn, the tensions (shrinking forces) of elastic members adhered to sheet materials covering a front part and a back part are required not to differ. Since this makes it unlikely for the front part and the back part to be wrinkled, the disposable wearing article can look nicer to improve the product value thereof.

In order to meet the above requirements, an object of the present invention is to provide a method for producing disposable wearing articles that can reduce the production costs and improve the product value.

SUMMARY OF THE INVENTION

According to an aspect of the present invention, an elastic strip material is produced by sandwiching an elastic member between two webs under a stretched state in the longitudinal direction of the webs, and is halved in the widthwise direction so that protrusions and recesses alternately appear. A halved first elastic strip material and a halved second elastic strip material are separated in the widthwise direction. Predetermined parts of the first and second elastic strip materials are made to have a reduced shrinking force, and an absorber is attached onto the predetermined parts of the first and second elastic strip materials to thereby produce a disposable wearing article.

This method can ensure reduction in the production costs and improve the product value.

BRIEF DESCRIPTION OF THE DRAWINGS

FIGS. 9A and 9B show disposable underpants of a first embodiment, wherein FIG. 9A is a plan view in its developed state, FIG. 9B is a sectional view in side thereof.

FIGS. 10A and 10B show disposable underpants of a second embodiment, wherein FIG. 10A is a plan view showing a first and a second elastic strip materials in step 3 and FIG. 10B is a plan view showing the disposable underpants in a developed state.

FIGS. 11A and 11B show disposable underpants of a third embodiment, wherein FIG. 11A is a plan view of an absorber and FIG. 11B is a plan view of the disposable underpants in a developed state.

FIGS. 12A and 12B show disposable underpants of a fourth embodiment, wherein FIG. 12A is a plan view showing a first elastic strip material and a second elastic strip material in step 3 and FIG. 12B is a plan view showing the disposable underpants in a developed state.

BEST MODE FOR CARRYING OUT THE INVENTION

Hereinafter, embodiments of the present invention are described in detail with reference to the accompanying drawings.

FIGS. 13A to 13D are plan views showing disposable wearing articles of the pants type (hereinafter, referred to as "disposable underpants") 1A to 1D in their developed states.

Figure 14A:
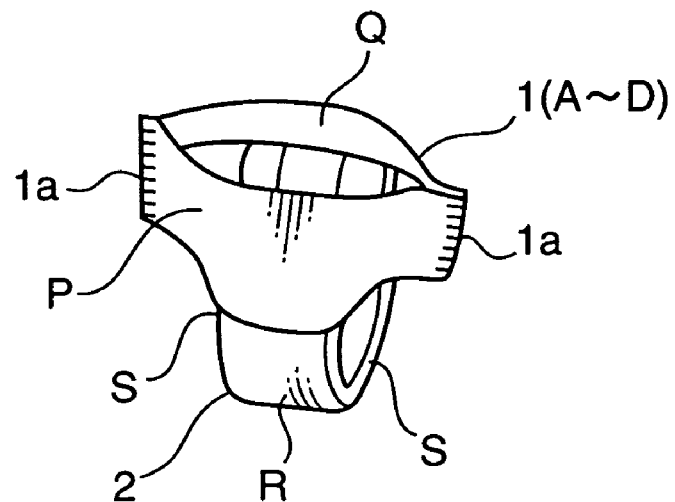
FIG. 14A is a perspective view of disposable underpants and FIG. 14B is a plan view showing the point of an S-cut of the elastic strip material.

In each pair of disposable underpants 1A to 1D, an absorber 2 is fixed across a front part (first elastic strip material) P and a back part (second elastic strip material) Q. The absorber 2 is folded to place the front part P and the back part Q one over the other and opposite side portions 1a of the front part P and the back part Q are sealed as shown in FIG. 14A, whereby each pair of disposable underpants 1A to 1D come to take a pant shape.

In the disposable underpants 1A to 1D, a crotch part R is formed by the absorber 2 and openings S for legs are formed at the opposite sides of this absorber 2.

Figure 13A:
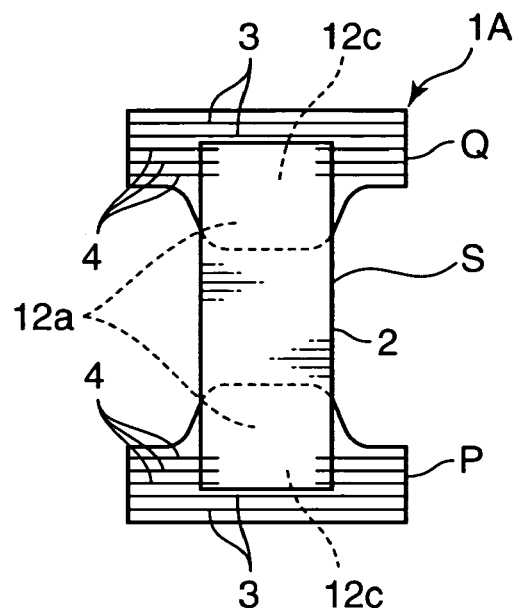
FIGS. 13A to 13D are schematic plan views of the disposable underpants of the first to fourth embodiments.
Figure 13B:
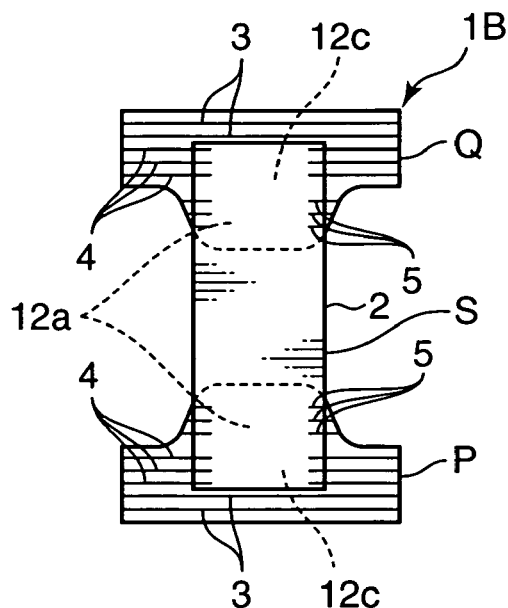
Figure 13C:
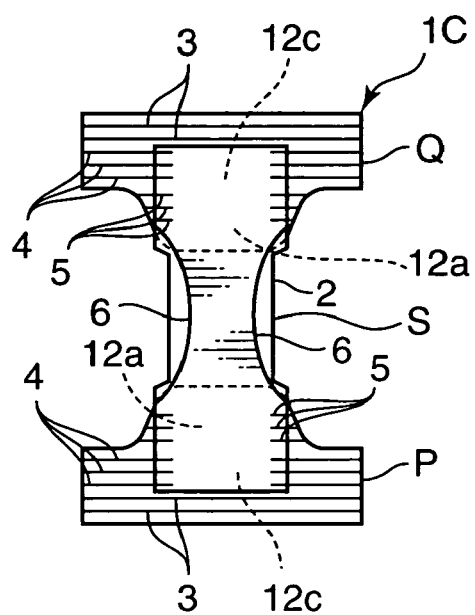
Figure 14B:
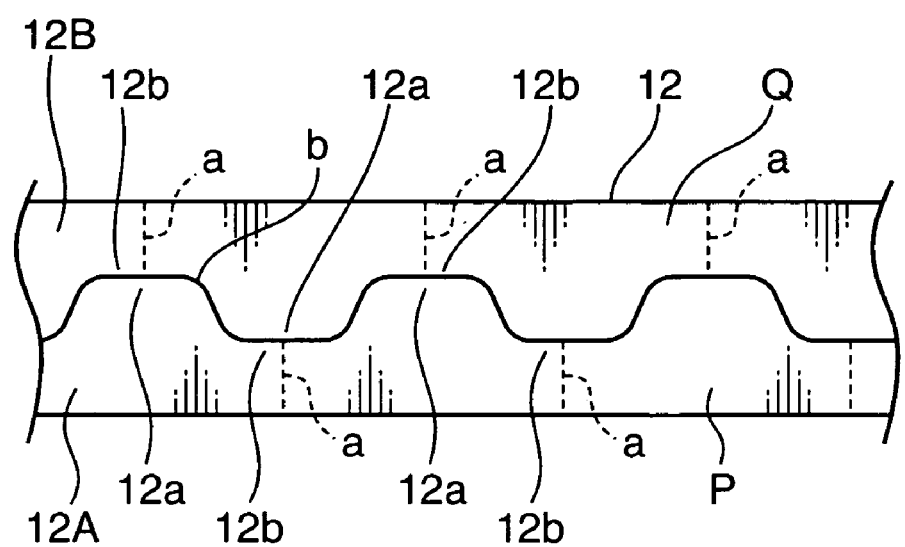

The summary of the production procedure of the disposable underpants 1A to 1C shown in FIGS. 13A to 13C is described with reference to FIG. 14B. In order to facilitate the description, the description of this production procedure does not necessarily coincide with that of production steps 1 to 15 to be described later.

First, an elastic strip material 12 is cut into two in the widthwise direction along a cutting line "b" so that protrusions 12a and recesses 12b alternately appear; a first and a second elastic strip materials 12A, 12B obtained by halving the elastic strip material 12 are cut along cutting lines "a" to produce the front parts P and the back parts Q, and are displaced along longitudinal direction so that the protrusions 12a and the recesses 12b become in phase and separated along widthwise direction; and each absorber 2 is fixed across both protrusions 12a.

Figure 13D:
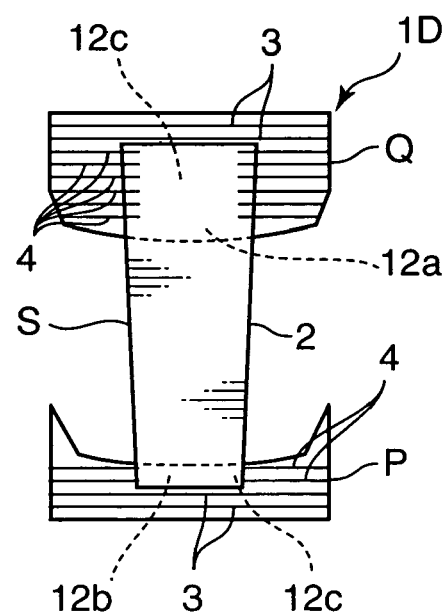

The disposable underpants 1D of FIG. 13D are obtained by separating the first and second elastic strip materials 12A, 12B along the widthwise direction without displacing the phases and by attaching the absorber 2 onto the protrusion 12a and the recess 12b.

In the disposable underpants 1A of the first embodiment shown in FIG. 13A, elastic members 3 for waist and elastic members 4 for body fitting are adhered to the front part P and the back part Q, and the absorber 2 is fixed across parts 12c near the protrusions 12a where the shrinking forces of the elastic members 4 for body fitting are reduced.

In the disposable underpants 1B of the second embodiment shown in FIG. 13B, elastic members 3 for waist, elastic members 4 for body fitting and elastic members 5 for around legs are adhered to the front part P and the back part Q, and the absorber 2 is fixed across parts 12c near the protrusions 12a where the shrinking forces of the elastic members 4 for body fitting and the elastic members 5 for around legs are reduced.

The disposable underpants 1C of the third embodiment shown in FIG. 13C are obtained by adhering elastic members 6 for legs to the opposite sides of the absorber 2 of the disposable underpants 1B of FIG. 13B.

In the disposable underpants 1D of the fourth embodiment shown in FIG. 13D, elastic members 3 for waist and elastic members 4 for body fitting are adhered to the front part P and the back part Q, and the absorber 2 is fixed across parts 12c near the protrusion 12a and the recess 12b where the shrinking forces of the elastic members 4 for body fitting are reduced.

Next, a method for producing the disposable underpants 1A of the first embodiment shown in FIG. 13A as a representative example is described with reference to FIGS. 1 to 8.

Steps 1 to 4 are steps for producing the first and second elastic strip materials 12A, 12B from the elastic strip material 12 while the elastic strip material 12 runs in the transverse direction.

Figure 1:
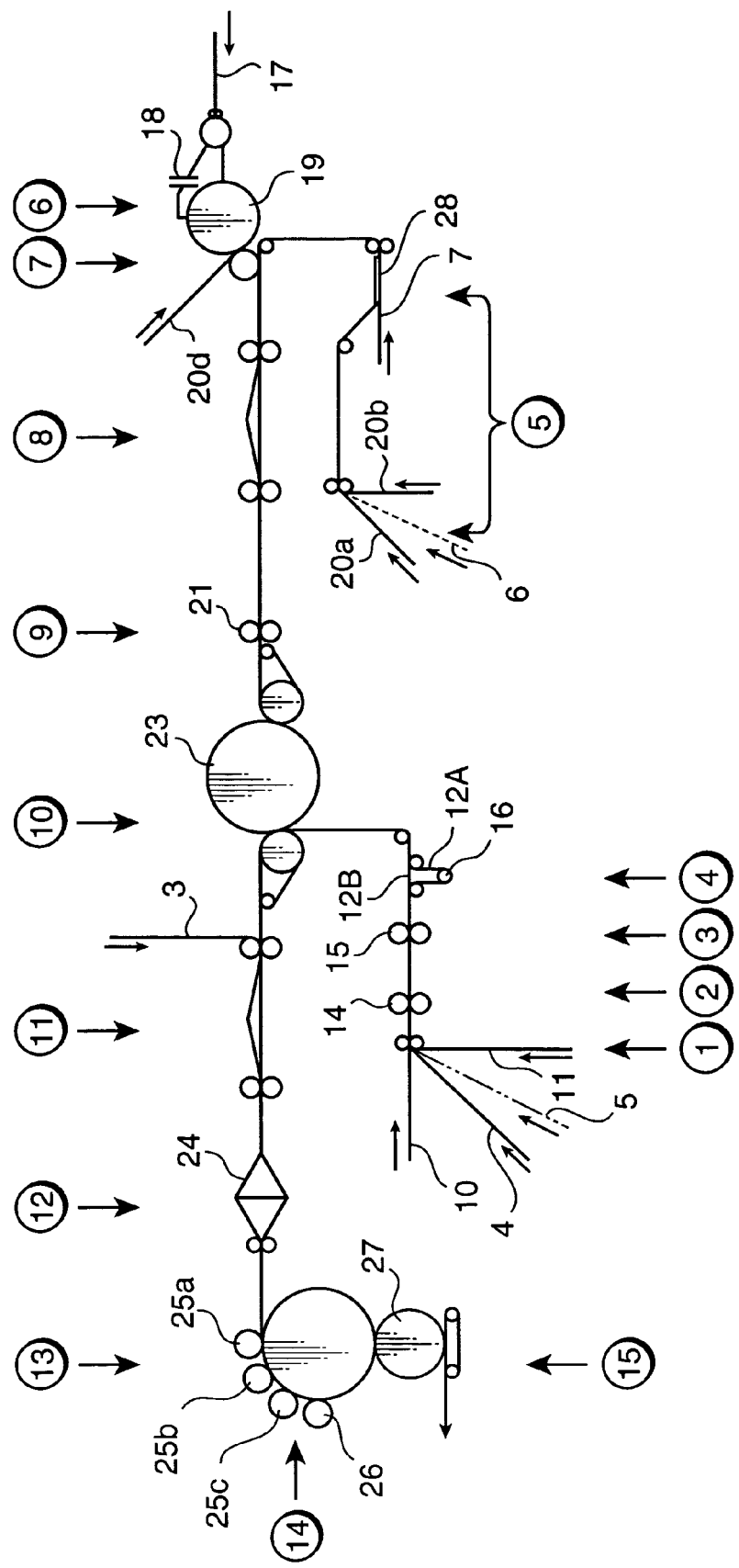
FIG. 1 is a system diagram of a production process for disposable underpants.
Figure 2:
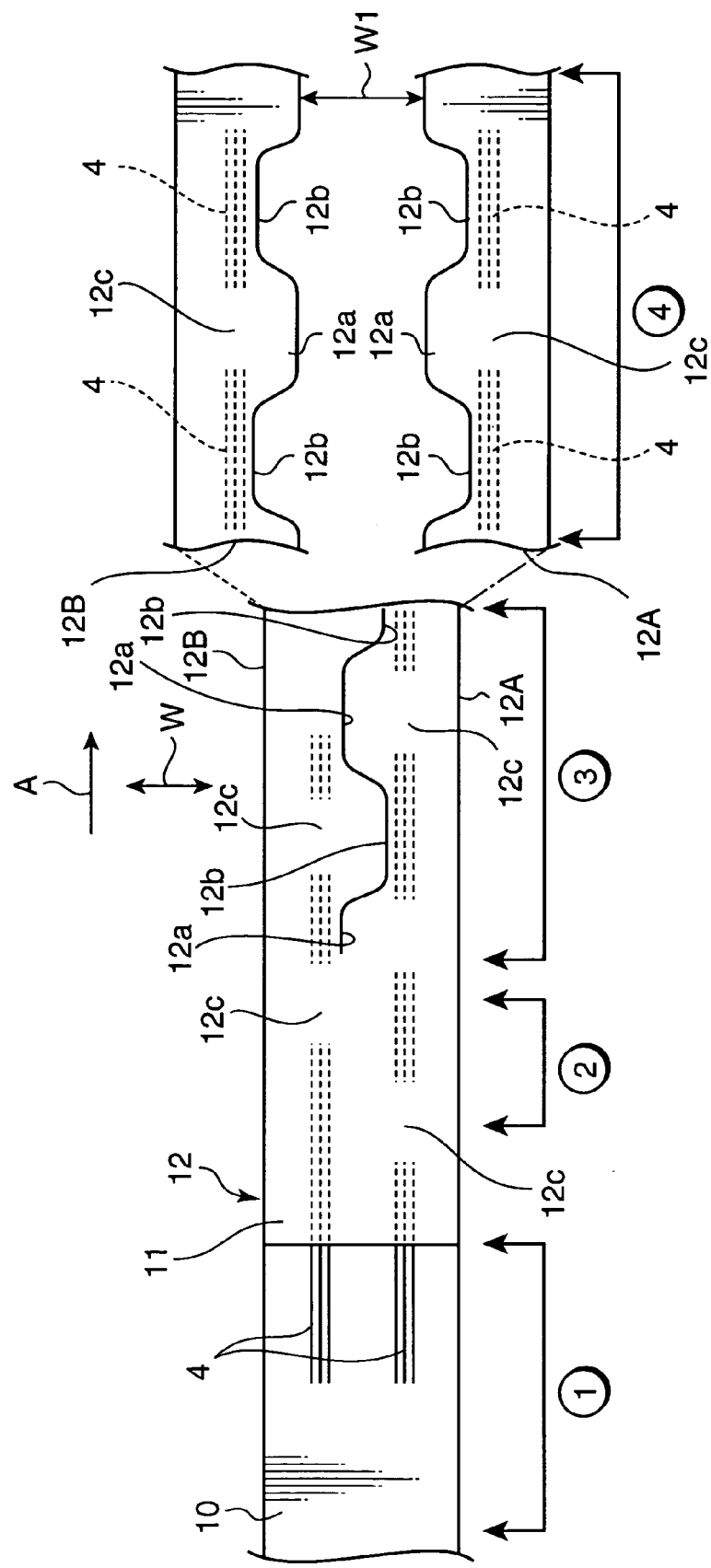
FIG. 2 is a plan view showing states of production in steps 1 to 4.
Figure 6A:
FIGS. 6A to 6D are sectional views showing essential portions of the states of production in steps 1 to 4.
Figure 6B:
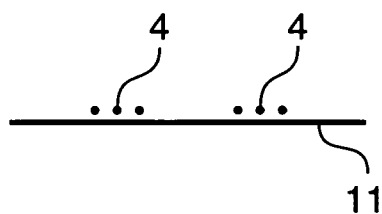
Figure 6C:
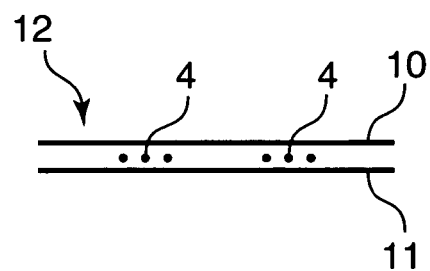

[Step 1] With reference to FIGS. 1, 2 and 6, the elastic members 4 for body fitting for the front parts P and the back parts Q are sandwiched between an outer web 10 and an inner web 11 both made of nonwoven fabric and continuously fed in the longitudinal direction A while being stretched in the longitudinal direction A, thereby producing the elastic strip material 12 (see FIGS. 6A to 6C).

An adhesive such as a hot melt adhesive is applied to at least one of the webs 10, 11, which are adhered to each other while sandwiching the elastic members 4 for body fitting therebetween.

Polyurethane, natural rubber, thermoplastic resin or the like can be used as the material for the elastic members 4 for body fitting, and the elastic members 4 may take the shape of a thread, a ribbon or the like. One elastic member 4 may be used or a plurality of elastic members 4 may be used together. In the case of using a thermoplastic resin as the material, the use of the hot melt adhesive may be unnecessary if the thermoplastic resin itself has a function of adhering the webs 10, 11. It should be noted that the respective elastic members 3, 5 to 7 to be described later are made of similar material and take similar shapes.

[Step 2] The elastic strip material 12 is cut into two, i.e., the first and second elastic strip materials 12A, 12B in the widthwise direction so that the protrusions (flap portions around legs) and the recesses 12b alternately appear in step 3 to be described next. Such a treatment as to reduce the shrinking forces of the elastic members 4 for body fitting near the protrusions 12a of the first and second elastic strip materials 12A, 12B is applied in preceding step 2, thereby forming the parts 12c having reduced shrinking forces.

For a treatment to reduce the shrinking forces, there can be adopted a method for melting the elastic members 4 for body fitting, for example, using an embossing roll (heat embossing) (see Japanese Unexamined Patent Publication No. 2002-113042) or a method for cutting the elastic members 4 for body fitting by a gather cutter 14. It is preferable to melt or cut the elastic members 4 for body fitting while the elastic strip material 12 is caused to extend along the roll by being vacuum-pulled.

Step of reducing the shrinking forces may be implemented any time up to later-described step 10 of attaching the absorber 2.

[Step 3] The elastic strip material 12 is cut into two in the widthwise direction W by an S-cutter 15 so that the protrusions 12a and the recesses 12b alternately appear in the elastic strip material 12 (so-called S-cutting), thereby producing the first and second elastic strip materials 12A, 12B.

Figure 6D:
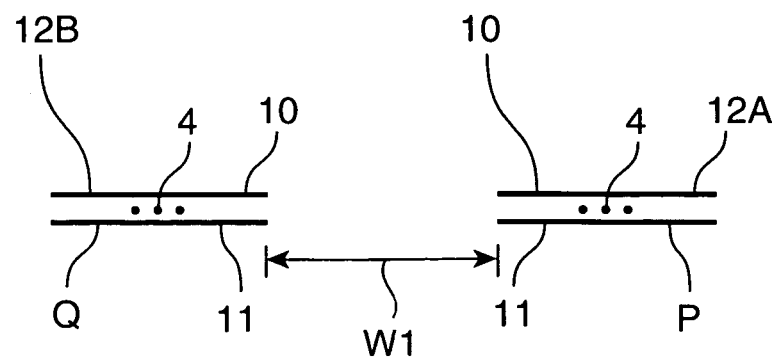

[Step 4] The first and second elastic strip materials 12A, 12B obtained by the halving are separated in the widthwise direction W to have a specified spacing W1, and the phases thereof are shifted in the longitudinal direction A so that the protrusions 12a and the recesses 12b become in phase (see FIG. 6D). It is sufficient for the first and second elastic strip materials 12A, 12B to be separated until the absorbers 2 are adhered after the so-called S-cutting.

As a method for shifting the phases, a continuous feeding distance of the first elastic strip material 12A in the longitudinal direction A may be made longer than that of the second elastic strip material 12B in the longitudinal direction A. Specifically, the feeding distance can be made longer by feeding the first elastic strip material 12A along a dummy roll 16.

Steps 5 to 9 are steps for producing the absorbers 2 while the absorbers 2 run along their longitudinal direction.

Figure 3:
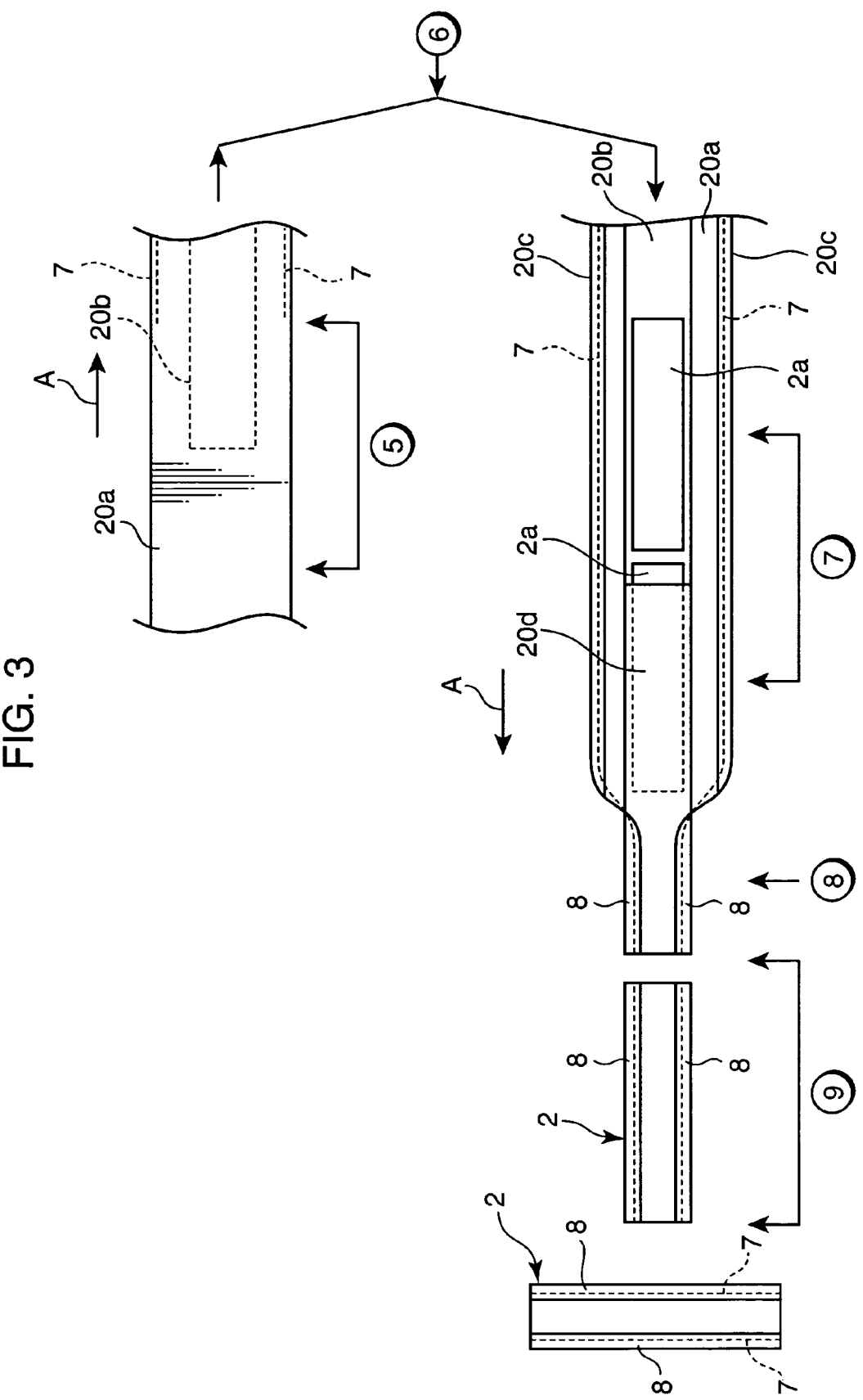
FIG. 3 is a plan view showing states of production in steps 5 to 9.
Figure 4:
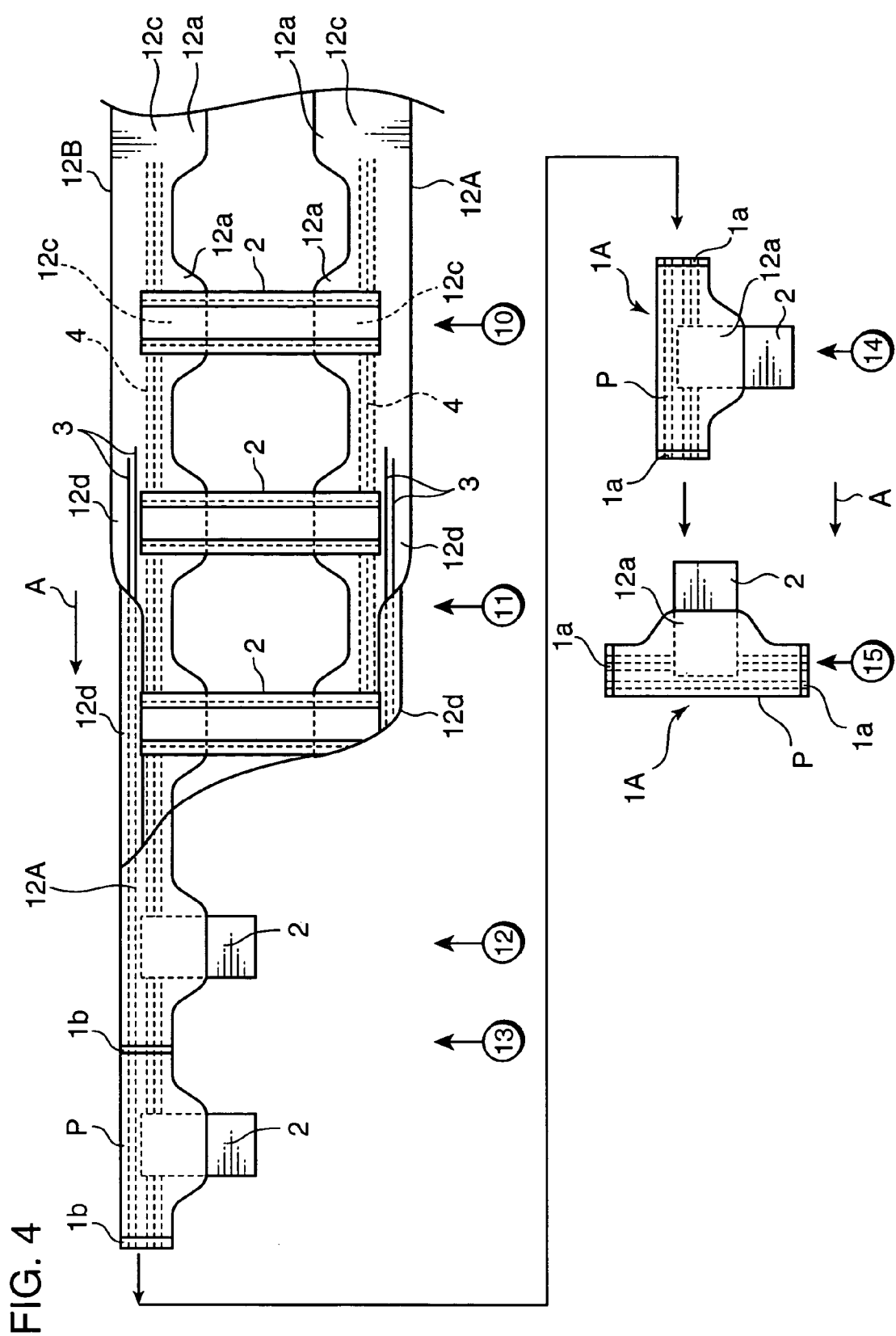
FIG. 4 is a plan view showing states of production in steps 10 to 15.
Figure 5:
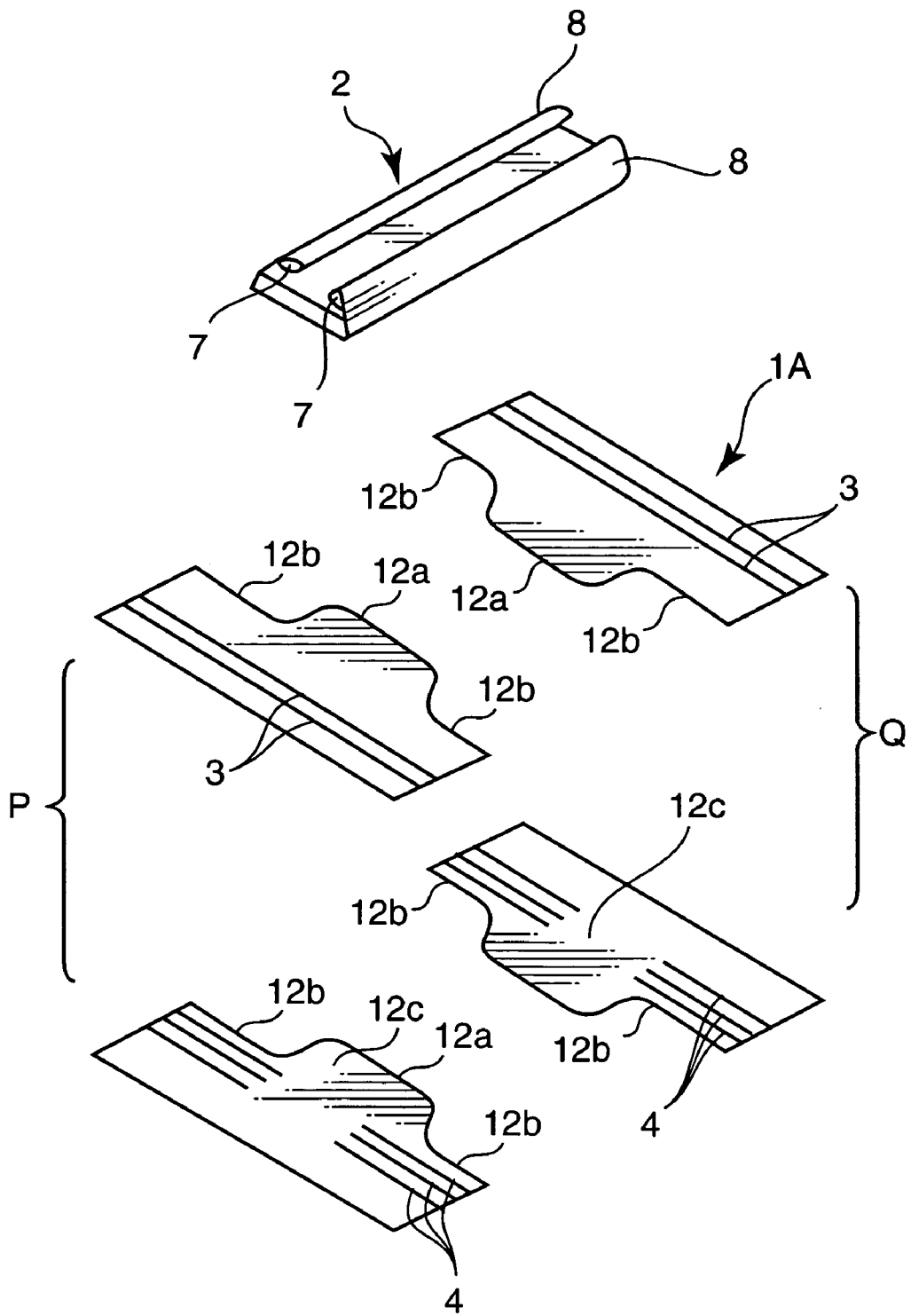
FIG. 5 is an exploded perspective view of disposable underpants.
Figure 7A:
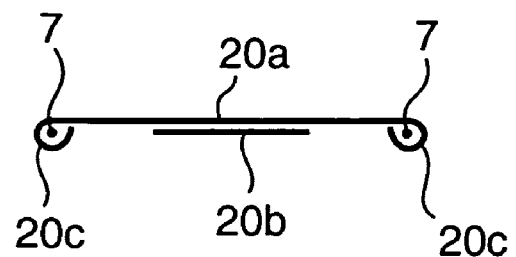
FIGS. 7A to 7D are sectional views showing essential portions of the states of production in steps 5 to 9.
Figure 7B:
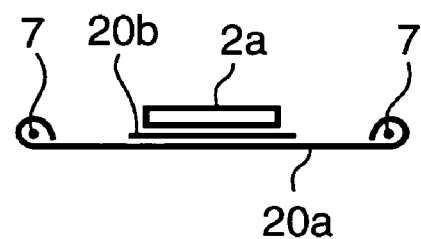
Figure 7C:
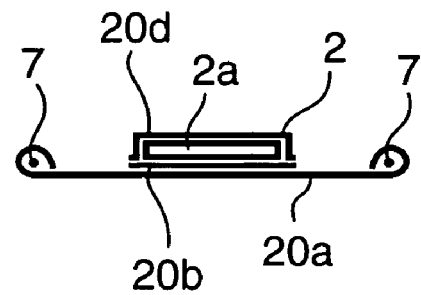
Figure 7D:
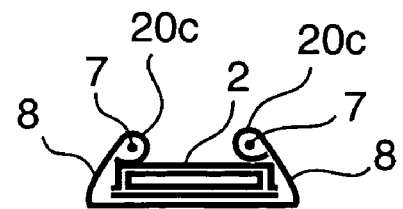

[Step 5] With reference to FIGS. 1, 3 and 7, a wider backing sheet 20a made of a nonwoven fabric and a liquid impermeable narrower backing sheet 20b continuously fed in the longitudinal direction A are adhered using a hot melt adhesive or the like, and elastic members 7 for flaps are adhered in inwardly curved portions 20c obtained by inwardly curving the opposite widthwise ends of the wider backing sheet 20b by means of a sealer 28 while being stretched in the longitudinal direction A (see FIG. 7A). The liquid impermeable sheet is preferably a polyethylene sheet or a water-repellant and breathing nonwoven fabric. The backing sheet 20a may be a liquid impermeable sheet and the backing sheet 20b may be a liquid permeable sheet, or both backing sheets 20a, 20b may be liquid impermeable sheets. In other words, it is sufficient to prevent a liquid leakage from a core 2a of the absorber 2 by the backing sheet(s).

[Step 6] The cores 2a of the absorbers 2 are formed by a method for placing fluff obtained by crushing a roll pulp 17 by a crusher 18 (see Japanese Unexamined Patent Publication No. S63-139547) while being let to run along their transverse direction. It should be noted that a high water-absorbent polymer may be mixed with the fluff.

In the case of producing the cores 2a while letting them to run in their transverse direction, the orientation of the cores 2a are turned by 90° by means of a repitch turn drum (see International Publication No. WO01/44086).

[Step 7] The backing sheets 20a, 20b produced in step 5 are U-turned to vertically invert them, the cores 2a running along their longitudinal direction are placed on the backing sheet 20b located above (see FIG. 7B), and a liquid permeable top sheet 20d is adhered to the backing sheet 20b together with the core 2a using a hot melt adhesive or the like (see FIG. 7C), whereby the absorber 2 elongated in the longitudinal direction A is produced. The liquid permeable sheet is preferably a liquid permeable nonwoven fabric or a mesh sheet.

[Step 8] The inwardly-curved portions 20v at the opposite ends of the backing sheet 20a located at a lower side are folded inwardly (see FIG. 7D), thereby forming standing flaps 8. Instead of forming the standing flaps 8 using the backing sheet 20a or 20b, they may be formed using the top sheet 20d. In such a case, parts of the top 20d that serve as the standing flaps are preferably waterproofed.

[Step 9] The absorber 2 elongated in the longitudinal direction A is cut together with the standing flaps 8 to a specified length by an inner-side cutter 21, thereby producing rectangular absorbers 2.

Steps 10 to 15 are steps for assembling the disposable underpants 1A running along their transverse direction.

[Step 10] The absorber 2 produced in step 9 has its orientation turned by 90° by an inner-side turn drum 23 so as to run along its transverse direction (see left end of FIG. 3).

Figure 8A:
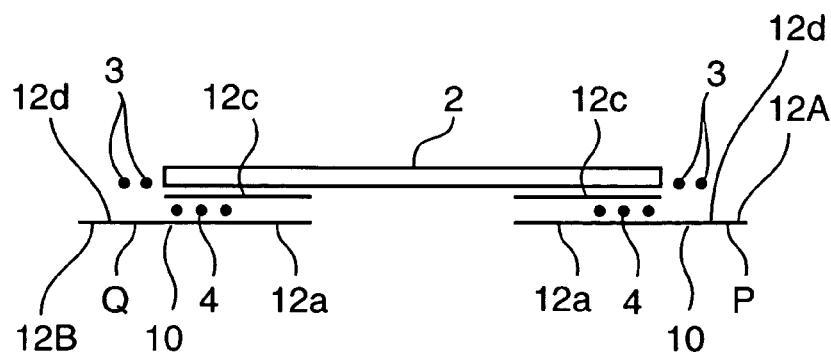
FIGS. 8A to 8C are sectional views showing essential portions of the states of production in steps 10 to 15.

On the other hand, the first and second elastic strip materials 12A, 12B produced in step 4 and being fed in transverse direction are U-turned to be vertically inverted, and the absorbers 2 are adhered across the parts 12c near the protrusions 12a of the first and second elastic strip materials 12A, 12B where the shrinking forces are reduced (see FIG. 8A).

Figure 8B:
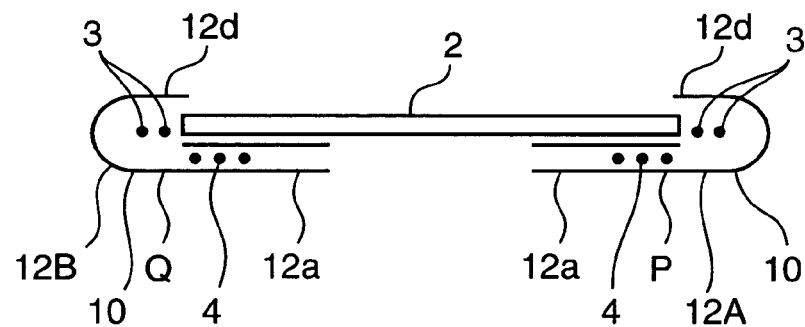

[Step 11] The elastic members 3 for waist are stretched in the longitudinal direction A at opposite widthwise end portions 12d of the outer web 10 of each of the first and second elastic strip materials 12A, 12B, and these end portions 12d are folded inwardly to adhere the elastic members 3 for waist within the opposite end portions 12d (see FIG. 8B). These opposite end portions 12d are also so adhered to the front and rear end portions of the absorber 2 as to cover the front and rear end portions of the absorber 2.

Figure 8C:
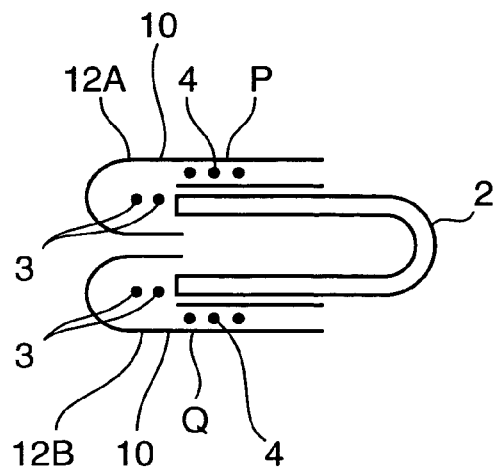

[Step 12] The absorber 2 is doubled with a middle position along widthwise direction W as a boundary by a doubling device 24 so that the first elastic strip material 12A comes to be located at an upper side and the second elastic strip material 12B comes to be located at a lower side (see FIG. 8C).

[Step 13] The first and second elastic strip materials 12A, 12B placed one over the other are melted for side sealing at middle positions (portions of the recesses 12b and corresponding to the opposite sides 1a of the disposable underpants 1A) between adjacent absorbers 2 by a plurality of heat sealers 25a to 25c. It is not always necessary to provide a plurality of heat sealers 25a to 25c. Instead of using the heat sealers 25a to 25c, side sealing may be carried out by ultrasonic waves.

[Step 14] By cutting middle portions of portions 1b, to which side sealing was applied, by means of a product cutter 26, the disposable underpants 1A having the opposite side portions 1a thereof sealed are completed.

[Step 15] The disposable underpants 1A as a product are conveyed to a product checking step and to a packing step after being turned by 90° by a product inverter 27.

Among steps 1 to 15, the elastic strip material 12 is halved in the widthwise direction, and the absorber 2 is adhered across the first and second elastic strip materials 12A, 12B with the divided first and second elastic strip materials 12A and 12B obtained by the halving separated along widthwise direction W in step 3. Thus, no trim (loss part) is produced even if the webs 10, 11 are cut in the production process. Therefore, the production cost of the disposable underpants 1A can be reduced.

Upon wearing the disposable underpants 1A produced by halving the elastic strip material 12 sandwiching the elastic members 4 for body fitting (elastic members 5 for around legs if necessary) at the same tension between the two webs 10, the front part P and the back part Q are unlikely to be wrinkled since the tensions (shrinking forces) of the elastic members 4, 5 of the front part P and the back part Q do not differ. Therefore, the disposable underpants 1A look nicer and the product value thereof can be improved.

In step 3 of halving the elastic strip material 12 in the widthwise direction, the elastic strip material 12 is so cut that the protrusions 12a and the recesses 12b alternately appear. In following step 4, the phases of the first and second elastic strip materials 12A, 12B obtained by the halving are shifted in the longitudinal direction A so that the protrusions 12a and the recesses 12b become in phase, and the first and second elastic strip materials 12A, 12B are separated along widthwise direction W, whereby the absorbers 2 can be fixed across the both protrusions 12a of the first and second elastic strip materials 12A, 12B. Since the absorbers 2 can be fixed to the protrusions 12a having a large space, the attaching can be securely carried out.

Further, since parts of the absorber 2 can be covered by the both protrusions 12a of the first and second elastic strip materials 12A, 12B, the absorber 2 approximates to the shape of the pants. Therefore, the disposable underpants look nicer and the product value thereof can be improved.

Further, the shrinking forces are unlikely to act on the absorber 2 by attaching the absorber 2 onto the parts near the protrusions 12a of the first and second elastic strip materials 12A, 12B where the shrinking forces are reduced. Thus, the absorber 2 is unlikely to shrink due to the shrinking forces, therefore the property of being closely fitting to the body can be improved.

Figure 9A:
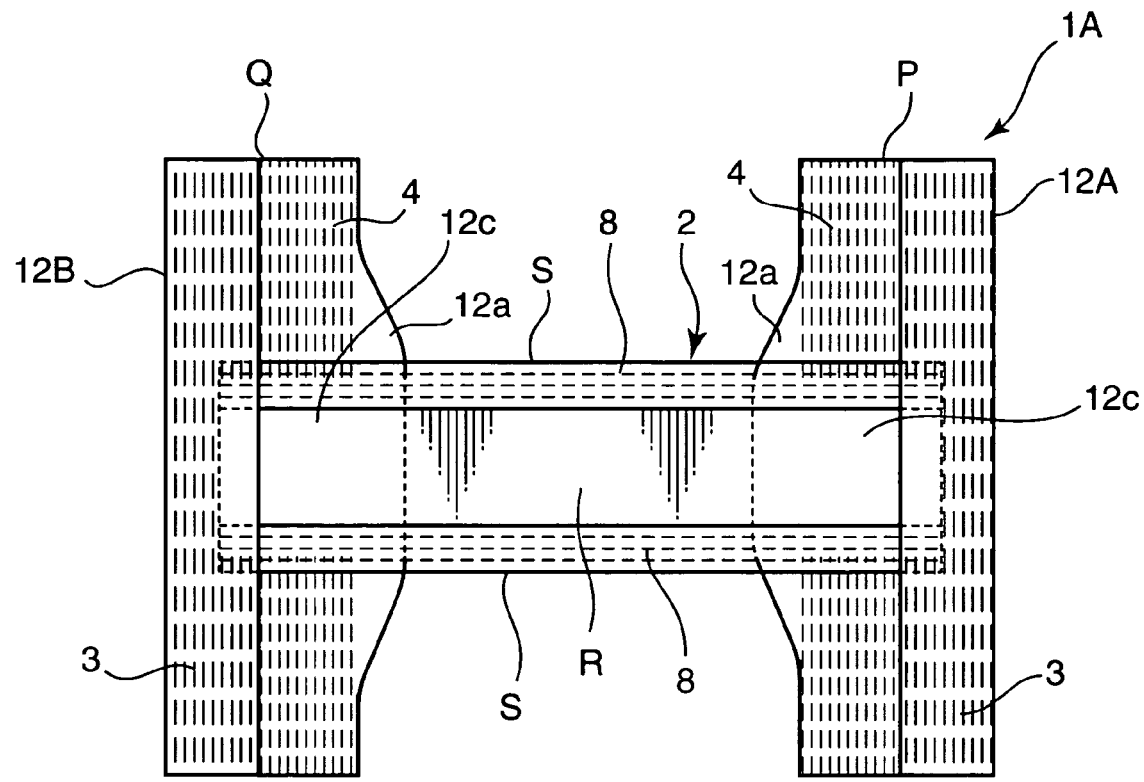
Figure 9B:
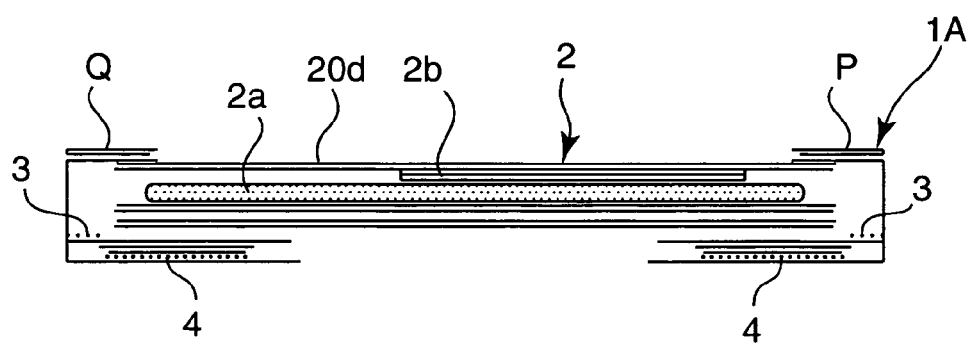

FIGS. 9A and 9B show the specifically commercialized disposable underpants 1A of the first embodiment corresponding to FIG. 13A, wherein FIGS. 9A and 9B are a plan view and a side view in section of the disposable underpants 1A in a developed state. It should be noted that a body fluid dispersing sheet 2b is provided between the core 2a and the top sheet 20d.

Figure 10A:
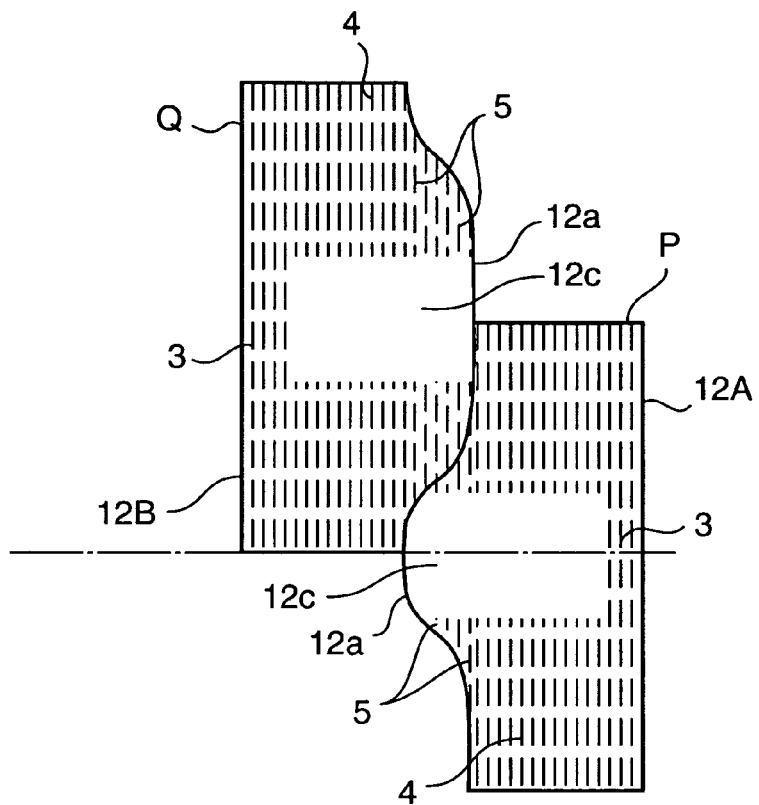
Figure 10B:
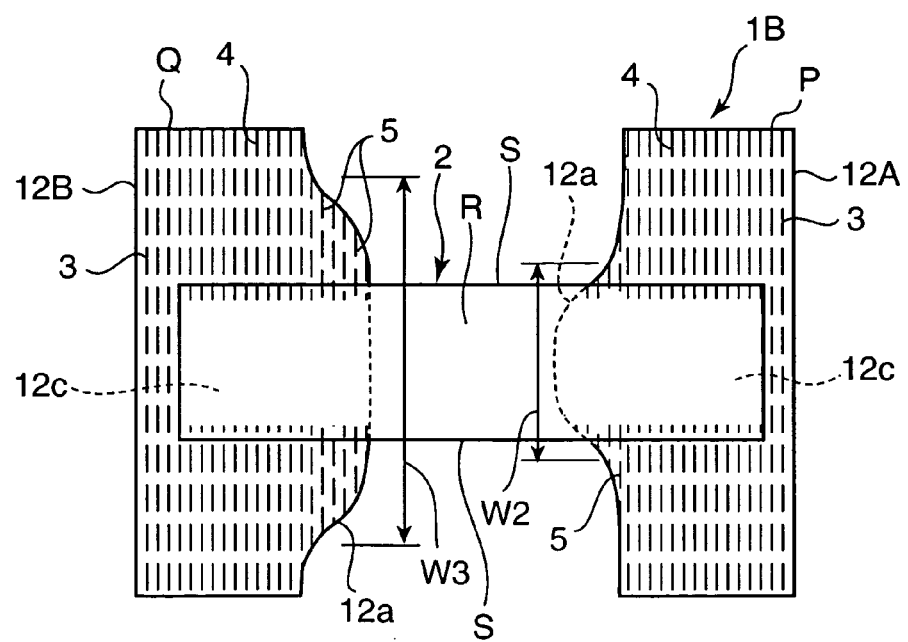

FIGS. 10A and 10B show the specifically commercialized disposable underpants 1B of the second embodiment corresponding to FIG. 13B, wherein FIG. 10A is a plan view showing the first and second elastic strip materials 12A, 12B in step 3 and FIG. 10B is a plan view showing the disposable underpants 1B in a developed state.

A first point of difference from the disposable underpants 1A of FIG. 9 is that width W2 of the protrusions 12a of the first elastic strip material 12A is narrowed while width W3 of the protrusions 12a of the second elastic strip material 12B is widened by cutting in step 2. Since the width W2 of the protrusion 12a of the front part P is narrower, the crotch part of the front part P is not wrinkled when the disposable underpants 1B are worn. Further, since the width W2 of the protrusion 12a of the back portion Q is wider, the buttocks can be widely covered when the disposable underpants 1B are worn. This can make the disposable underpants 1B look nicer to improve the product value of the wearing article.

A second point of difference from the disposable underpants 1A of FIG. 9 is that the elastic members 5 for around legs are sandwiched under a stretched state in the respective protrusions 12a of the first and second elastic strip materials 12A, 12B.

The elastic members 5 for around legs can be simultaneously sandwiched when the elastic members 4 for body fitting are sandwiched along the longitudinal direction A of the webs 10, 11 under a stretched state between the outer web 10 and the inner web 11 in step 1 (see FIG. 1). This enables the protrusions 12a to be better fitted to the legs of the body.

In step 2, upon applying the treatment to reduce the shrinking forces of the elastic members 4 for body fitting near the respective protrusions 12a of the first and second elastic strip materials 12A, 12B, a treatment to reduce the shrinking forces of the elastic members 5 for around legs may also be applied, whereby the parts 12c having even reduced shrinking forces can be formed.

Figure 11A:
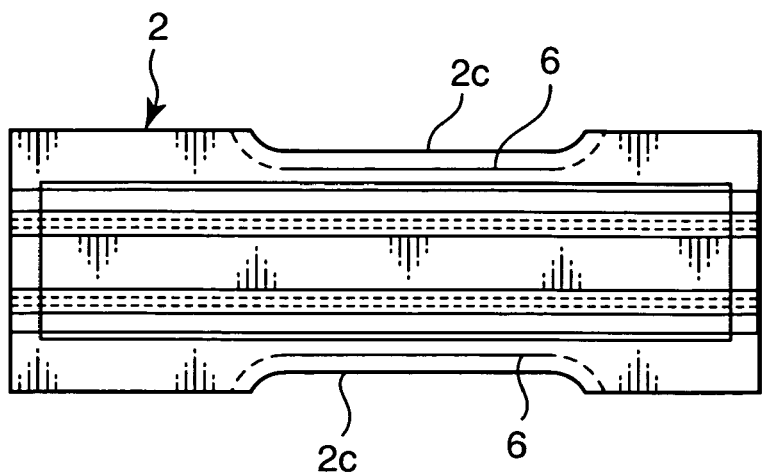
Figure 11B:
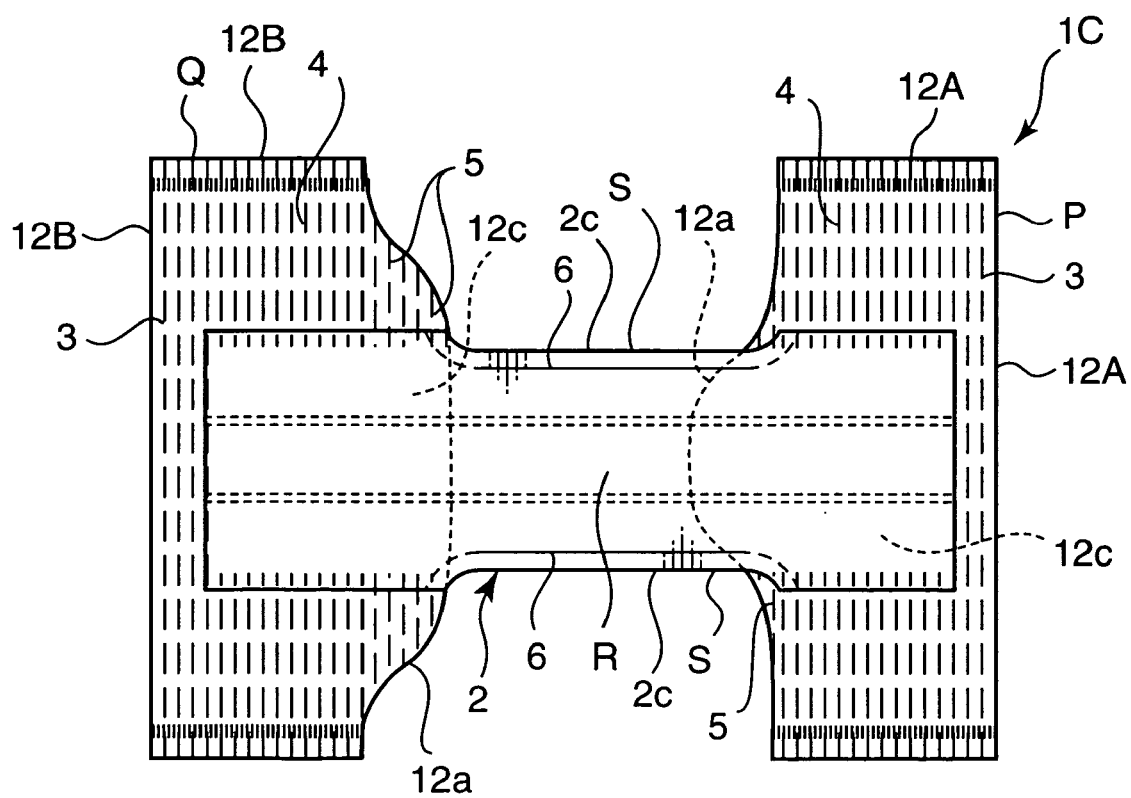

FIGS. 11A and 11B show the specifically commercialized disposable underpants 1C of the third embodiment corresponding to FIG. 13C, wherein FIG. 11A is a plan view of the absorber 2 and FIG. 11B is a plan view showing the disposable underpants 1C in a developed state.

The disposable underpants 1C are basically the same as the disposable underpants 1B of FIG. 10, but differ therefrom in that hollows 2c are formed at the opposite sides of the absorber 2 and the elastic members 6 for legs are adhered along the hollows 2c.

The elastic members 6 for legs can be sandwiched between the backing sheets 20a, 20b under a stretched state before the backing sheets 20a, 20b are adhered using the hot melt adhesive or the like in step 5 (see FIG. 1).

Since the hollows 2c of the absorber 2 are continuous with the outer contour lines of the respective protrusions 12a of the first and second elastic strip materials 12A, 12B, the hollows 2c fit well around the legs of the body. In addition, the disposable underpants 1C can be held in close contact with the crotch part of the body at the opposite sides of the absorber 2 by the elastic members 6 for legs as well as by the elastic members 5 for around legs.

Figure 12A:
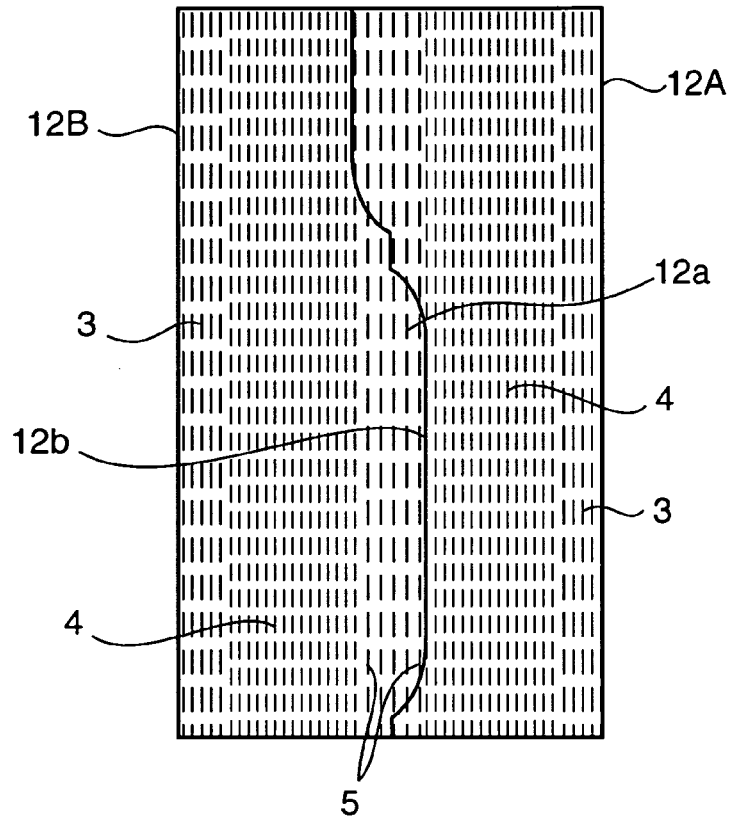
Figure 12B:
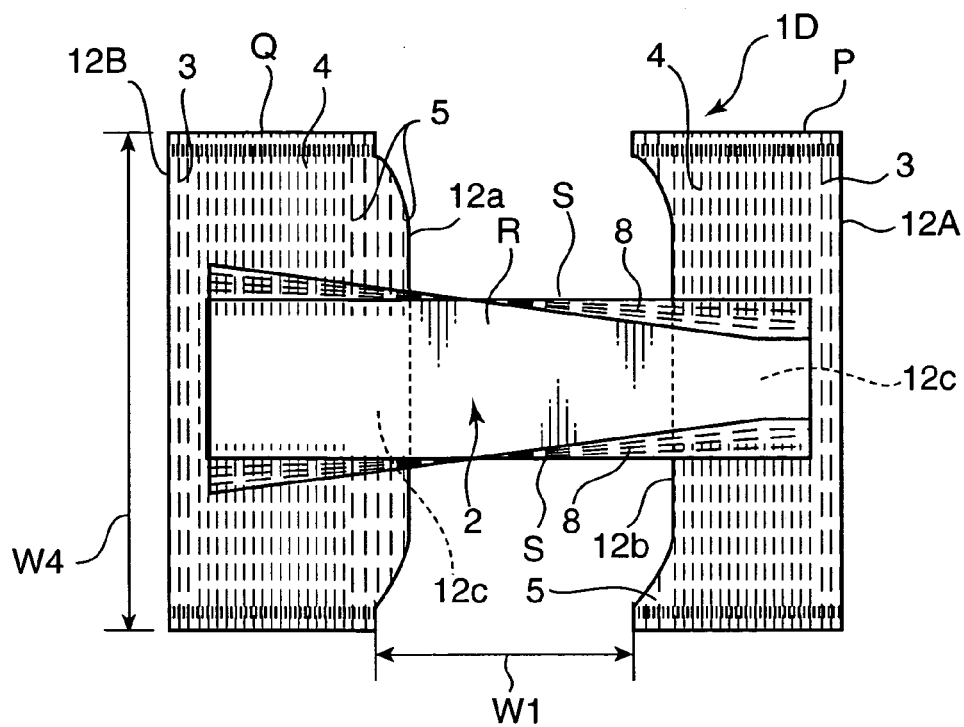

FIGS. 12A and 12B show the specifically commercialized disposable underpants 1D of the fourth embodiment corresponding to FIG. 13D, wherein FIG. 12A is a plan view showing the first and second elastic strip materials 12A, 12B in step 3 and FIG. 12B is a plan view showing the disposable underpants 1D in a developed state.

The disposable underpants 1D are basically the same as the disposable underpants 1B of FIG. 10. A first point of difference is that the protrusion 12a and the recess 12b are formed to take moderate curved lines over the entire width W4 of the disposable underpants 1D upon producing the first and second elastic strip materials 12A, 12B in step 3.

A second point of difference from the disposable underpants 1B of FIG. 10 is that the first and second elastic strip materials 12A, 12B are merely separated by a specified distance W1 in the widthwise direction W in step 4 without shifting them by half the phase in the longitudinal direction A so that the protrusion 12b and the recess 12b become in phase (see FIG. 6D).

With the disposable underpants 1D, the production process can be simplified since a part of step 4 for shifting the phases is unnecessary.

A third point of difference from the disposable underpants 1B of FIG. 10 is that the absorber 2 is not rectangular; a side thereof at the side of the front part P takes a narrower trapezoidal shape while a side thereof at the back part Q takes a wider trapezoidal shape; the standing flaps 8 are tuned inwardly at the side of the front part P while being turned outwardly at the side of the back part Q.

The back part widened by this twisting of the standing flaps 8 and the wider back part Q of the absorber 2 can more effectively prevent a lateral leakage, particularly, from the side of the back part Q.

As described above, an inventive method for producing disposable wearing articles, comprises the steps of producing an elastic strip material by sandwiching an elastic member between two webs under a stretched state in the longitudinal direction of the webs; halving the elastic strip material in the widthwise direction so that protrusions and recesses alternately appear; separating a first elastic strip material and a second elastic strip material obtained by halving in the widthwise direction thereof; reducing the shrinking force of the elastic member near predetermined parts of the first and second elastic strip materials; and attaching an absorber onto the respective predetermined parts of the first and second elastic strip materials where the shrinking force is reduced.

It may be appreciated to shift the phases of the first and second elastic strip materials in the longitudinal direction thereof so that the protrusions and the recesses become in phase, and reduce the shrinking force of the elastic member near protrusions of the first and second elastic strip materials, and attach an absorber onto the respective protrusions of the first and second elastic strip materials where the shrinking force is reduced.

The elastic strip material is halved in the widthwise direction, and the first and second elastic strip materials obtained by the halving are separated in the widthwise direction with the phases thereof shifted in the longitudinal direction. In this state, the absorber is attached onto the first and second elastic strip materials. Thus, no trim or loss part is produced even if the webs are cut in the production process. However, the webs may be slightly cut in order to design the first and second elastic strip materials. In such a case, trims or loss parts are produced, although only a small amount.

Further, upon wearing the disposable wearing article produced by halving the elastic strip material produced by sandwiching the elastic member between the two webs at the same tension, the tensions or shrinking forces of the elastic members adhered to the sheet materials covering the front part and the back part do not differ.

In the step of halving the elastic strip material in the widthwise direction, the elastic strip material is so that the protrusions and the recesses alternately appear. In the succeeding step, the first and second elastic strip materials obtained by the halving have the phases thereof shifted in the longitudinal direction so that the protrusions and the recesses become in phase, and are separated in the widthwise direction, whereby the absorber can be attached onto the two protrusions of the first and second elastic strip materials.

Further, the two protrusions of the first and second elastic strip materials can cover parts of the absorber.

Furthermore, no shrinking force acts on the absorber by attaching the absorber onto the parts of the first and second elastic strip materials where the protrusions where the shrinking force is reduced.

Alternatively, an inventive producing method may comprise the steps of producing an elastic strip material by sandwiching an elastic member between two webs under a stretched state in the longitudinal direction of the webs; halving the elastic strip material in the widthwise direction so that protrusions and recesses alternately appear; separating a first elastic strip material and a second elastic strip material obtained by the halving in the widthwise direction; reducing the shrinking force of the elastic members near the protrusions of the first elastic strip material and the recesses of the second elastic strip material; and attaching an absorber onto parts of the first and second elastic strip materials where the shrinking force is reduced.

A point of difference of the latter producing method from the former one is that the phases of the first and second elastic strip materials obtained by the halving are not shifted in the longitudinal direction. This has an advantage of obviating the need for the step of shifting the phases, in addition to the functions and effects of the former producing method.

In the inventive producing method, the elastic member may be an elastic member for body fitting and the method may further comprise a step of adhering an elastic member for waist to the elastic strip material under a stretched state.

In the inventive producing method, the elastic member may include an elastic member for body fitting and an elastic member for around legs, and the method may further comprises a step of adhering an elastic member for waist to the elastic strip material under a stretched state.

The inventive producing method may further comprise a step of folding the absorber to place the first and second elastic strip materials one over the other and sealing the opposite side portions of the first and second elastic strip materials.

In the inventive producing method, standing flaps may be preferably provided at the opposite sides of the absorber.

In the inventive producing method, the standing flaps may be preferably so twisted as to be turned inward at the front side of the absorber and to be turned outward at the back side of the absorber.

In the inventive producing method, hollows may be preferably formed at the opposite sides of the absorber, and elastic members for legs are adhered along the hollows under a stretched state.

Accordingly, the elastic strip material is halved in the widthwise direction and the first and second elastic strip materials obtained by the halving are separated in the widthwise direction and have the phases thereof shifted. In this state, the absorbers are fixed across the first and second elastic strip materials. Thus, even if the webs are cut in the production process, no trim (loss part) is produced. Therefore, the production cost for the wearing articles can be reduced.

Further, by halving the elastic strip material formed by sandwiching the elastic members between the two webs at the same tension, the tensions (shrinking forces) of the elastic members adhered to the sheet materials covering the front part and the back part do not differ when the produced disposable wearing article is worn. Thus, the front part and the back part are unlikely to be wrinkled. Therefore, the wearing article can look nicer to improve the product value thereof.

In the step of halving the elastic strip material in the widthwise direction, the elastic strip material is cut such that the protrusions and the recesses alternately appear. In the succeeding step, the first and second elastic strip materials obtained by halving have the phases thereof shifted in the longitudinal direction so that the protrusions and the recesses become in phase, and are separated in the widthwise direction, whereby the absorber can be fixed across the two protrusions of the first and second elastic strip materials. Since this enables the absorber to be fixed to the protrusions having a large space, the attaching can be more securely carried out.

Further, since the two protrusions of the first and second elastic strip materials can cover parts of the absorber, the shape of the wearing article approximates to that of pants. Thus, the wearing article can look nicer to improve the product value thereof.

Furthermore, no shrinking force comes to act on the absorber by attaching it onto the parts near the protrusions of the first and second elastic strip materials where the shrinking forces are reduced. Thus, the absorber does not get shrunk due to the shrinking force, wherefore the absorber can be better fitted to the body.

The elastic members for body fitting can effectively prevent the wearing article from slipping down from the body when the wearing article is worn.

The elastic members for body fitting can effectively prevent the wearing article from slipping down from the body when the wearing article is worn and the elastic members for around legs enable the wearing article to be better fitted to the legs of the body.

The wearing article can be made to be of the pants type.

The standing flaps can effectively prevent a lateral leakage from the opposite sides of the absorber.

Since the back side of the absorber is widened by the twisting of the standing flaps, a lateral leakage, particularly from the back side can be effectively prevented.

The opposite sides of the absorber can fit around the legs of the body by the hollows, and can be held in closer contact with the crotch part of the body.

What is claimed is:

1. A method for producing a disposable wearing article, comprising the steps of:

producing an elastic strip material by sandwiching two elastic members between two webs under a stretched state in a longitudinal direction of the webs in such a way that the elastic members are at positions apart from a widthwise center of the webs;

halving the elastic strip material in a center area between the elastic members so that protrusions and recesses alternately appear to thereby define a first elastic strip and a second elastic strip;

separating the first elastic strip and the second elastic strip from each other in a widthwise direction;

shifting the first elastic strip from the second elastic strip in the longitudinal direction so that the protrusions of the first and second elastic strips come into the same phase to define aligned pairs of protrusions, the protrusions in each of the aligned pairs of protrusions being spaced apart in the widthwise direction;

attaching absorbers onto respective predetermined parts of the first and second elastic strips so that the absorbers lie over the protrusions in each of the pairs of the first and second elastic strips;

wherein after or before the step of halving the elastic strip material, less shrinking force parts are formed on the two elastic members at portions corresponding to the respective protrusions of the first and second elastic strips.

2. A method according to claim 1, the method further comprising a step of adhering an elastic member for waist to the elastic strip material under a stretched state.

3. A method according to claim 1, further comprising a step of folding each absorber to place the first and second elastic strip materials one over the other and sealing the opposite side portions of the first and second elastic strip materials.

4. A method according to claim 1, wherein standing flaps are provided at the opposite sides of each absorber.

5. A method according to claim 4, wherein the standing flaps are so twisted as to be turned inward at the front side of each absorber and to be turned outward at the back side of each absorber.

6. A method according to claim 1, wherein opposite sides of the absorber are concave, and an elastic member for legs is adhered in the longitudinal direction of the absorber along the opposite sides of each absorber under a stretched state.

7. A method for producing a disposable wearing article, comprising:

providing two elongate webs, each of the webs having opposite first and second edges extending along a longitudinal direction of the respective web and a longitudinally extending central region between the first and second edges;

sandwiching first and second elastic members between the two webs so that the elastic members are stretched in the longitudinal direction of the webs, the first elastic members being between the first edges and the longitudinal central regions of the webs and the second elastic members being between the second edges and the longitudinal central regions of the webs, the webs and the elastic members producing an elastic strip material, the elastic members being arranged so that selected areas along the elastic strip material exhibit reduced elastic restoring forces;

forming an undulating cut through the elastic strip material so that the undulating cut alternately approaches and retracts from the edges;

separating the elastic strip material on opposite sides of the undulating cut to define first and second elastic strips, each of said first and second elastic strips having longitudinally spaced protrusions formed by the undulating cut, the protrusions substantially corresponding to the areas of reduced elastic restoring forces;

shifting the first elastic strip longitudinally and laterally so that the protrusions of the first elastic strip align with the protrusions of the second elastic strip while being spaced laterally therefrom; and attaching absorbers to the first and second elastic strips so that each absorber overlies two of the aligned protrusions on the first and second elastic strips.

8. A method of claim 7, wherein the step of sandwiching first and second elastic members between the two webs comprises sandwiching first and second waist elastic members between the webs at locations in proximity to the respective first and second sides.

9. The method of claim 7, further comprising the step of adhering leg elastic members to each absorber along edges of the absorber extending substantially transverse to the edges of the webs.

10. The method of claim 7, wherein the step of sandwiching first and second elastic members between the webs comprises sandwiching a plurality of first elastic members at longitudinally spaced positions and sandwiching a plurality of second elastic members at longitudinally spaced positions, the longitudinally spaced first elastic members being at least partly offset in the longitudinal direction from the plurality of second elastic members.

11. The method of claim 10, wherein the step of forming an undulating cut comprises forming the cut so that undulations of the cut approach the respective longitudinally spaced first and second elastic members.

12. The method of claim 7, further comprising a step of folding each absorber so that the respective first edges substantially register with the respective second edges of the webs.

13. The method of claim 12, further comprising sealing the first and second elastic strips to one another at locations between the protrusions.

14. The method of claim 12, further comprising cutting the first and second elastic strips between the protrusions that are longitudinally adjacent to one another.

* * * * *